(12) United States Patent
Feret et al.

(10) Patent No.: US 9,050,416 B2
(45) Date of Patent: Jun. 9, 2015

(54) NEEDLE SAFETY DEVICE WITH FLOATING RING

(71) Applicant: Tech Group Europe Limited, Dublin (IE)

(72) Inventors: Alain Feret, Evreux (FR); Philippe Chabert, Bourneville (FR); Jean Paul Crepel, Neauphle-le-Chateau (FR); Alain Mazurie, Bihorel (FR)

(73) Assignee: TECH GROUP EUROPE LIMITED, Dublin (IE)

( * ) Notice: Subject to any disclaimer, the term of this patent is extended or adjusted under 35 U.S.C. 154(b) by 361 days.

(21) Appl. No.: 13/666,588

(22) Filed: Nov. 1, 2012

(65) Prior Publication Data

US 2014/0121605 A1    May 1, 2014

(51) Int. Cl.
*A61M 5/32*    (2006.01)

(52) U.S. Cl.
CPC ............ *A61M 5/3245* (2013.01); *A61M 5/3257* (2013.01)

(58) Field of Classification Search
CPC .......................... A61M 5/3245; A61M 5/3257
USPC ......................................................... 604/198
See application file for complete search history.

(56) References Cited

U.S. PATENT DOCUMENTS

| | | |
|---|---|---|
| 1,921,034 A | 8/1933 | La Marche |
| 3,880,163 A | 4/1975 | Ritterskamp |
| 4,631,057 A | 12/1986 | Mitchell |
| 4,723,943 A | 2/1988 | Spencer |
| 4,747,831 A | 5/1988 | Kulli |
| 4,828,548 A | 5/1989 | Walter |
| 4,832,696 A | 5/1989 | Luther et al. |
| 4,871,355 A | 10/1989 | Kikkawa |

(Continued)

FOREIGN PATENT DOCUMENTS

| | | |
|---|---|---|
| EP | 0904792 A2 | 3/1999 |
| EP | 0966983 A1 | 12/1999 |

(Continued)

OTHER PUBLICATIONS

Int'l Preliminary Report on Patentability issued Dec. 12, 2013 in Int'l Application No. PCT/US2012/039385.
Office Action issued Jul. 18, 2014 in U.S. Appl. No. 14/009,814 by Chevalier.
Office Action issued Oct. 24, 2013 in U.S. Appl. No. 11/861,567 by Pessin.

(Continued)

*Primary Examiner* — Kevin C Sirmons
*Assistant Examiner* — Deanna K Hall
(74) *Attorney, Agent, or Firm* — Panitch Schwarze Belisario & Nadel LLP

(57) ABSTRACT

A needle safety device includes a sleeve having proximal and distal portions separated by a radially-inwardly projecting ledge. A ring in the proximal portion is movable between a first position spaced from the ledge, and a second position adjacent to or abutting the ledge. A shield with at least one radially deformable tab receives the syringe and is movable in the sleeve between an initial position with the tab adjacent to or abutting the ledge, an injection position with the tab spaced from the ledge, and a protection position with the tab located distally from the ledge. The tab, during movement between initial and injection positions, deforms inwardly and traverses the inner surface of the ring, and during movement between injection and protection positions, translates with the ring from the first to the second position, and subsequently deforms inwardly and traverses the inner surface of the ring and the ledge.

18 Claims, 9 Drawing Sheets

(56) References Cited

U.S. PATENT DOCUMENTS

| | | | |
|---|---|---|---|
| 4,887,998 A | 12/1989 | Martin et al. |
| 4,911,693 A | 3/1990 | Paris |
| 4,923,447 A | 5/1990 | Morgan |
| 4,927,416 A | 5/1990 | Tomkiel |
| 4,929,237 A | 5/1990 | Medway |
| 4,931,040 A | 6/1990 | Haber et al. |
| 4,943,282 A | 7/1990 | Page et al. |
| 4,966,592 A | 10/1990 | Burns et al. |
| 4,986,819 A | 1/1991 | Sobel |
| 5,026,349 A | 6/1991 | Schmitz et al. |
| 5,106,379 A | 4/1992 | Leap |
| 5,108,378 A | 4/1992 | Firth et al. |
| 5,112,307 A | 5/1992 | Haber et al. |
| 5,141,500 A | 8/1992 | Hake |
| 5,163,918 A | 11/1992 | Righi et al. |
| 5,201,708 A | 4/1993 | Martin |
| 5,201,720 A | 4/1993 | Borgia et al. |
| 5,261,880 A | 11/1993 | Streck et al. |
| 5,267,972 A | 12/1993 | Anderson |
| 5,279,581 A | 1/1994 | Firth et al. |
| 5,346,480 A | 9/1994 | Hess et al. |
| 5,360,410 A | 11/1994 | Wacks |
| 5,380,296 A | 1/1995 | Smedley et al. |
| 5,411,487 A | 5/1995 | Castagna |
| 5,501,672 A | 3/1996 | Firth et al. |
| 5,531,706 A | 7/1996 | de la Fuente |
| 5,558,651 A | 9/1996 | Crawford et al. |
| 5,573,513 A | 11/1996 | Wozencroft |
| 5,591,138 A | 1/1997 | Vaillancourt |
| 5,601,536 A | 2/1997 | Crawford et al. |
| 5,803,918 A | 9/1998 | Vetter et al. |
| 5,817,064 A | 10/1998 | DeMarco et al. |
| 5,855,839 A | 1/1999 | Brunel |
| 5,891,104 A | 4/1999 | Shonfeld et al. |
| 5,891,105 A | 4/1999 | Mahurkar |
| 5,913,846 A | 6/1999 | Szabo |
| 5,989,226 A | 11/1999 | Hymanson |
| 5,997,513 A | 12/1999 | Smith et al. |
| 6,013,059 A | 1/2000 | Jacobs |
| 6,033,386 A | 3/2000 | Novacek et al. |
| 6,086,566 A | 7/2000 | Arnissolle |
| 6,159,184 A | 12/2000 | Perez et al. |
| 6,171,284 B1 | 1/2001 | Kao et al. |
| 6,186,980 B1 | 2/2001 | Brunel |
| 6,296,625 B1 | 10/2001 | Vetter et al. |
| 6,319,233 B1 | 11/2001 | Jansen et al. |
| 6,319,234 B1 | 11/2001 | Restelli et al. |
| 6,344,032 B1 | 2/2002 | Perez et al. |
| 6,416,323 B1 | 7/2002 | Grenfell et al. |
| 6,419,658 B1 | 7/2002 | Restelli et al. |
| 6,475,194 B2 | 11/2002 | Domici, Jr. et al. |
| 6,547,764 B2 | 4/2003 | Larsen et al. |
| 6,565,540 B1 | 5/2003 | Perouse et al. |
| 6,569,115 B1 | 5/2003 | Barker et al. |
| 6,585,702 B1 | 7/2003 | Brunel |
| 6,613,022 B1 | 9/2003 | Doyle |
| 6,623,459 B1 | 9/2003 | Doyle |
| 6,685,676 B2 | 2/2004 | Jansen et al. |
| 6,719,730 B2 | 4/2004 | Jansen et al. |
| 6,918,889 B1 | 7/2005 | Brunel |
| 6,949,086 B2 | 9/2005 | Ferguson et al. |
| 6,966,898 B1 | 11/2005 | Pouget et al. |
| 6,997,901 B2 | 2/2006 | Popovsky |
| 7,029,461 B2 | 4/2006 | Ferguson et al. |
| 7,097,636 B2 | 8/2006 | Pessin |
| 7,144,389 B2 | 12/2006 | Ferguson et al. |
| 7,300,421 B1 | 11/2007 | Lowry et al. |
| 7,429,256 B2 | 9/2008 | Chevallier et al. |
| 7,582,073 B2 | 9/2009 | Barrelle et al. |
| 7,678,086 B2 | 3/2010 | Chevallier |
| 7,699,814 B2 | 4/2010 | Lande |
| 7,824,379 B2 | 11/2010 | Doyle |
| 7,875,006 B2 | 1/2011 | Pessin |
| 7,938,808 B2 | 5/2011 | Pessin |
| 8,118,787 B2 | 2/2012 | Chevallier et al. |
| 8,192,407 B2 | 6/2012 | Pessin |
| 2001/0031949 A1 | 10/2001 | Asbaghi |
| 2001/0039401 A1 | 11/2001 | Ferguson et al. |
| 2002/0002354 A1 | 1/2002 | Vetter et al. |
| 2002/0045864 A1 | 4/2002 | Perez et al. |
| 2002/0068921 A1 | 6/2002 | McWethy et al. |
| 2002/0156426 A1 | 10/2002 | Gagnieux et al. |
| 2002/0161337 A1 | 10/2002 | Shaw et al. |
| 2002/0193746 A1 | 12/2002 | Chevallier |
| 2003/0050607 A1 | 3/2003 | Gagnieux et al. |
| 2003/0229314 A1 | 12/2003 | McWethy et al. |
| 2004/0015137 A1 | 1/2004 | Hohlfelder et al. |
| 2004/0144668 A1 | 7/2004 | Marshall et al. |
| 2004/0193120 A1 | 9/2004 | Ferguson et al. |
| 2004/0236283 A1 | 11/2004 | Tang |
| 2004/0267206 A1 | 12/2004 | Rimlinger et al. |
| 2005/0020985 A1 | 1/2005 | Doyle |
| 2005/0080383 A1 | 4/2005 | Woehr |
| 2005/0119623 A1 | 6/2005 | Pessin |
| 2005/0148933 A1 | 7/2005 | Raven et al. |
| 2005/0148943 A1 | 7/2005 | Chevalier |
| 2005/0165353 A1 | 7/2005 | Pessin |
| 2006/0184133 A1 | 8/2006 | Pessin |
| 2006/0200077 A1 | 9/2006 | Righi et al. |
| 2006/0264887 A1 | 11/2006 | Lande |
| 2007/0088287 A1 | 4/2007 | Chevallier |
| 2007/0179441 A1 | 8/2007 | Chevallier |
| 2007/0239117 A1 | 10/2007 | Chelak et al. |
| 2008/0021409 A1 | 1/2008 | Pessin |
| 2008/0208140 A1 | 8/2008 | Barrelle |
| 2008/0294120 A1 | 11/2008 | Chevallier et al. |
| 2008/0312603 A1 | 12/2008 | Chevallier et al. |
| 2009/0105661 A1 | 4/2009 | Chevallier et al. |
| 2010/0217205 A1 | 8/2010 | Chevallier et al. |
| 2012/0022465 A1 | 1/2012 | Stamp et al. |
| 2012/0095408 A1 | 4/2012 | Eaton et al. |

FOREIGN PATENT DOCUMENTS

| | | | |
|---|---|---|---|
| EP | 1 066 848 A2 | 1/2001 |
| EP | 1474194 A1 | 11/2004 |
| EP | 1532997 A1 | 5/2005 |
| EP | 1235603 B1 | 5/2006 |
| FR | 2653667 A1 | 5/1991 |
| FR | 2762790 A1 | 11/1998 |
| FR | 2794650 A1 | 12/2000 |
| FR | 2807665 A1 | 10/2001 |
| FR | 2830764 A1 | 4/2003 |
| FR | 2830765 A1 | 4/2003 |
| FR | 2835753 A1 | 8/2003 |
| FR | 2837107 A1 | 9/2003 |
| FR | 2860162 A1 | 4/2005 |
| FR | 2861598 A1 | 5/2005 |
| FR | 2922455 A1 | 4/2009 |
| JP | H05-500621 T | 2/1993 |
| JP | H08-010324 A | 1/1996 |
| JP | H09-502893 T | 3/1997 |
| JP | 2843677 B2 | 1/1999 |
| JP | H11-319090 A | 11/1999 |
| JP | 2003-501218 A | 1/2003 |
| JP | 2003-511106 A | 3/2003 |
| JP | 2004-528075 T | 9/2004 |
| JP | 2005-516741 T | 6/2005 |
| JP | 2006-505340 A | 2/2006 |
| WO | 9426334 A1 | 11/1994 |
| WO | 9835714 A1 | 8/1998 |
| WO | 99 17823 A1 | 4/1999 |
| WO | 0124856 A1 | 4/2001 |
| WO | 0130427 A1 | 5/2001 |
| WO | 0137898 A2 | 5/2001 |
| WO | 0141841 A2 | 6/2001 |
| WO | 0185239 A2 | 11/2001 |
| WO | 02072182 A1 | 9/2002 |
| WO | 02089878 A1 | 11/2002 |
| WO | 03068298 A1 | 8/2003 |
| WO | 03/077977 A2 | 9/2003 |
| WO | 2004043524 A1 | 5/2004 |

(56) References Cited

FOREIGN PATENT DOCUMENTS

| WO | 2004087242 A1 | 10/2004 |
|---|---|---|
| WO | 2005039678 A2 | 5/2005 |
| WO | 2006/027445 A1 | 3/2006 |

OTHER PUBLICATIONS

Int'l Search Report issued Dec. 12, 2012 in Int'l Application PCT/US2012/039385.
Office Action issued Jun. 16, 2014 in U.S. Appl. No. 10/576,938 by Chevalier.
Office Action issued Jun. 24, 2014 in U.S. Appl. No. 12/738,509 by Chevalier.
Japanese Office Action mailed Feb. 2, 2010 in Japanese Appln No. 2006-536115.
Office Action Issued Oct. 2, 2008 in U.S. Appl. No. 10/576,938.
Office Action Issued Jul. 21, 2009 in U.S. Appl. No. 10/576,938.
Preliminary Search Report Issued Jun. 21, 2004 in FR Application No. 0312327.
International Search Report and Written Opinion mailed Jun. 6, 2005 in Int'l Application No. PCT/FR2004/002654.
Office Action Issued Dec. 22, 2008 in EP Application No. 04817285.2.
Int'l Preliminary Report on Patentability Issued Jul. 27, 2006 in Int'l Application No. PCT/FR2004/002654.
Office Action dated Mar. 9, 2010 in U.S. Appl. No. 10/576,938.
Office Action issued Sep. 14, 2010 in Japanese Appl Ser No. 2006-536115.
Japanese Office Action mailed Mar. 16, 2010 in JP Appln No. 2006-537346.
Int'l Search Report and Written Opinion issued Dec. 22, 2011 in Int'l Application PCT/US2011/031053.
Office Action issued Mar. 28, 2007 in U.S. Appl. No. 10/550,524.
Int'l Search Report issued Sep. 22, 2004 in Int'l Application No. PCT/FR2004/000755.
Office Action issued Apr. 17, 2009 in U.S. Appl. No. 11/861,567.
Office Action issued Jan. 13, 2010 in U.S. Appl. No. 11/861,567.
Office Action issued Sep. 1, 2009 in JP Application No. 2006-505752.
Office Action issued Jun. 8, 2010 in JP Application No. 2006-505752.
Office Action issued Dec. 7, 2010 in JP Application No. 2006-505752.
Search Report Issued Jul. 9, 2009 in EP Application No. 08 166 632.3.
Search Report Issued Jun. 13, 2008 in FR Application No. 0758496.
Office Action issued Mar. 22, 2011 in U.S. Appl. No. 12/738,509.
Office Action issued Aug. 25, 2011 in U.S. Appl. No. 12/738,509.
Int'l Search Report issued May 11, 2009 in Int'l Application No. PCT/FR2008/051908; Written Opinion.
Search Report issued Jun. 17, 2008 in FR Application No. 0758497; Written Opinion.
Office Action issued Dec. 23, 2011 in CN Application No. 200880112730.3.
U.S. Appl. No. 14/009,814 by Chevallier, filed Oct. 4, 2013.
Int'l Preliminary Report on Patentability issued Oct. 8, 2013 in Int'l Application No. PCT/US2011/031053.
Office Action issued Dec. 18, 2006 in U.S. Appl. No. 10/507,913 by Pessin.
Office Action issued Sep. 7, 2007 in U.S. Appl. No. 10/507,913 by Pessin.
Office Action issued Dec. 17, 2008 in U.S. Appl. No. 10/507,913 by Pessin.
Office Action issued Oct. 8, 2009 in U.S. Appl. No. 10/507,913 by Pessin.
Office Action issued Apr. 23, 2009 in EP Application No. 04 818 444.4.
Office Action issued Nov. 23, 2010 in EP Application No. 04 818 444.4.
Office Action issued Apr. 17, 2013 in EP Application No. 04 818 444.4.
Int'l Search Report issued Sep. 11, 2003 in Int'l Application No. PCT/FR2003/000722.
Search Report and English translation of Written Opinion issued Jul. 9, 2009 in EP Application No. 08 166 632.3.
Office Action issued Apr. 21, 2005 in U.S. Appl. No. 10/995,035 by Pessin.
Office Action issued Oct. 5, 2005 in U.S. Appl. No. 10/995,035 by Pessin.
Office Action issued Sep. 28, 2010 in JP Application No. 2007-528915.
Office Action issued Sep. 6, 2011 in JP Application No. 2007-528915.
Int'l Search Report issued Jan. 3, 2006 in Int'l Application No. PCT/FR2005/001983.
Int'l Preliminary Report on Patentability issued Feb. 28, 2007 in Int'l Application No. PCT/FR2005/01983.
Int'l Search Report issued Jan. 25, 2006 in Int'l Application No. PCT/FR2005/001926.
Int'l Preliminary Report on Patentability issued Feb. 28, 2007 in Int'l Application No. PCT/FR2005/001926.
Office Action issued May 15, 2009 in U.S. Appl. No. 11/574,333 by Pessin.
Office Action issued Sep. 10, 2008 in U.S. Appl. No. 11/574,333 by Pessin.
Office Action issued Dec. 13, 2007 in U.S. Appl. No. 11/574,333 by Pessin.
Office Action issued Aug. 20, 2010 in U.S. Appl. No. 11/574,176 by Pessin.
Int'l Preliminary Report on Patentability issued Feb. 21, 2006 in Int'l Application No. PCT/FR2004/000755.
Search Report issued Mar. 4, 2004 in FR Application No. 0312642.
Int'l Search Report issued Apr. 4, 2005 in Int'l Application No. PCT/FR2004/002597.
Office Action issued Mar. 11, 2009 in U.S. Appl. No. 10/577,380 by Chevallier.
Office Action issued Feb. 16, 2012 in CN Application No. 200880112413.1.
Search Report and Written Opinion issued Jun. 13, 2008 in FR Application No. 0758495.
Int'l Search Report and Written Opinion issued May 11, 2009 in Int'l Application No. PCT/FR2008/051907.
Int'l Preliminary Report on Patentability issued Jun. 1, 2010 in Int'l Application No. PCT/FR2008/051907.
Office Action issued Mar. 22, 2011 in U.S. Appl. No. 12/738,422.
Office Action issued Aug. 18, 2011 in U.S Appl. No. 12/738,422.
Office Action issued Jul. 1, 2009 in U.S. Appl. No. 12/254,266 by Chevallier.
Office Action issued Feb. 4, 2010 in U.S. Appl. No. 12/254,266 by Chevallier.
Office Action issued Nov. 3, 2011 in U.S. Appl. No. 12/254,266 by Chevallier.
Office Action issued Apr. 23, 2012 in U.S. Appl. No. 12/254,266 by Chevallier.
Office Action issued May 10, 2013 in U.S. Appl. No. 12/254,266 by Chevallier.
Office Action issued Oct. 10, 2013 in U.S. Appl. No. 12/254,266 by Chevallier.
Int'l Preliminary Report on Patentability issued Jun. 1, 2010 in Int'l Application No. PCT/FR2008/051908.
Search Report issued Jun. 24, 2004 in FR Application No. 0312327.
Office Action issued Sep. 28, 2010 in JP Application No. 2007-528913.
Search Report issued Feb. 22, 2005 in EP Application No. 04 29 2750.
Office Action issued Nov. 28, 2006 in EP Application No. 04 292 750.
Office Action issued Mar. 11, 2008 in EP Application No. 04 292 750.
Office Action issued Sep. 11, 2009 in EP Application No. 05 792 448.
Int'l Preliminary Report on Patentability issued Oct. 17, 2013 in Int'l Application No. PCT/US2011/031053.
Office Action issued Dec. 3, 2014 in US Appl. No. 12/738,509 by Chevalier.
Office Action issued Jan. 8, 2015 in US Appl. No. 10/576,938 by Chevalier.

NEEDLE SAFETY DEVICE WITH FLOATING RING

BACKGROUND OF THE INVENTION

Embodiments of the present invention relate generally to needle safety devices, and more particularly, to passively activated needle safety devices utilizing a floating ring.

Safety devices for preventing accidental needle sticks to patients, doctors, medical personnel, and the like are known. Such devices typically include some form of sheath or shield that is actuated to cover the end of the needle before and/or following injection. A device that requires the user to actively actuate the sheath or shield is generally disfavored because the user may forget to put the device in place to protect the needle, thereby creating unnecessary risk. The actuation of the sheath or shield is therefore preferably passive, i.e., actuation occurs automatically upon some operation of the syringe necessary for administering the injection. For example, depression of the plunger of the syringe or removal of the needle from the skin of a patient may cause the sheath or shield to be actuated.

However, such passive needle safety devices tend to be complex and therefore expensive to manufacture and difficult to assemble. It is desirable to provide a needle safety device with a simple design that still allows for reliable passive actuation.

BRIEF SUMMARY OF THE INVENTION

Briefly stated, a preferred embodiment of the present invention comprises a needle safety device for a syringe having a barrel and a needle fitted to a distal end of the barrel. The device includes a hollow sleeve having a proximal portion and a distal portion. The proximal portion is separated from the distal portion by a radially-inwardly projecting ledge. A ring is disposed in the proximal portion of the sleeve and has an outer surface and an inner surface. The ring is movable with respect to the proximal portion of the sleeve in an axial direction between a first position wherein the ring is spaced from the projecting ledge, and a second position wherein the ring is adjacent to or abuts the projecting ledge. A hollow shield is configured to receive the syringe at least partially therein and has at least one radially deformable tab at a proximal end thereof. The shield is at least partially disposed in the sleeve and is movable in an axial direction with respect to the sleeve between an initial position wherein the at least one tab is adjacent to or abuts the projecting ledge, an injection position wherein the at least one tab is spaced from the projecting ledge, and a protection position wherein the at least one tab is located distally from the projecting ledge so that the shield covers the needle. The at least one tab is configured to (i) during movement between the initial position and the injection position, deform radially inwardly and traverse the inner surface of the ring in the first position, and (ii) during movement between the injection position and the protection position, translate with the ring from the first position to the second position, and subsequently deform radially inwardly and traverse the inner surface of the ring and the projecting ledge.

Another preferred embodiment of the present invention comprises a needle safety device for use with a syringe having a barrel and a cannula extending from the barrel. The needle safety device includes a body, a ring supported by the body and movable relative to the body, a shield supported by the body and movable between an initial retracted position and a final extended position relative to the body, at least one first latch member extending from the shield, and a spring in contact with both the body and the shield. The spring biases the shield toward the final extended position. In a first configuration, the shield is in the initial retracted position and the at least one first latch member engages the body to retain the shield against the bias of the spring. In a second configuration, contact of a distal end of the shield against an injection site moves the shield relative to the body, moving the at least one first latch member into engagement with the movable ring and releasing the at least one first latch member from engagement with the body. In a third configuration, with the distal end of the shield moved out of contact with the injection site, the spring moves the movable ring and shield relative to the body, with the movable ring holding the at least one first latch member to prevent the at least one first latch member from re-engaging the body. In a fourth configuration, the shield is moved by the spring into the final extended position covering the cannula.

BRIEF DESCRIPTION OF THE SEVERAL VIEWS OF THE DRAWINGS

The foregoing summary, as well as the following detailed description of a preferred embodiment of the invention, will be better understood when read in conjunction with the appended drawings. For the purpose of illustrating the invention, there are shown in the drawings an embodiment which is presently preferred. It should be understood, however, that the invention is not limited to the precise arrangements and instrumentalities shown.

In the drawings.

DETAILED DESCRIPTION OF THE INVENTION

Figure 1:
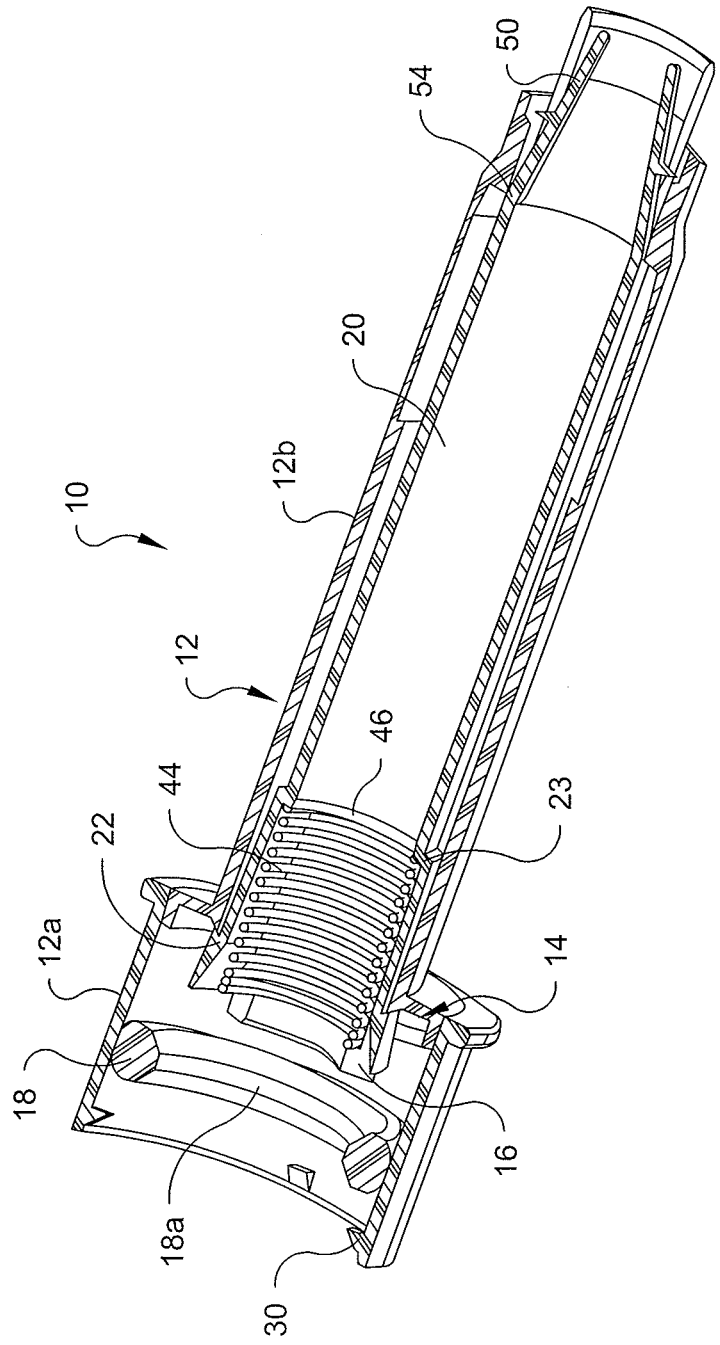
FIG. 1 is a cross-sectional perspective view of a needle safety device in accordance with a preferred embodiment of the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the needle safety device and designated parts thereof. Unless specifically set forth herein, the terms "a", "an" and "the" are not limited to one element but instead should be read as meaning "at least one". The terminology includes the words noted above, derivatives thereof and words of similar import.

Referring to the drawings, wherein the same reference numerals are used to designate the same components throughout the several figures, there is shown in FIG. 1 a needle safety device 10 in accordance with a preferred embodiment of the present invention. The needle safety device 10 includes a body preferably in the form of a hollow sleeve 12 having a proximal portion 12a and a distal portion 12b. The proximal and distal portions 12a, 12b are separated by a radially-inwardly projecting ledge 14. As shown in FIG. 1, the proximal and distal portions 12a, 12b are preferably formed from two separate pieces of a rigid polymeric material that may be coupled to one another by welding, adhesive, press-fit, fasteners, or the like. In this configuration, the ledge 14 can be formed by the material of one or both of the proximal and distal portions 12a, 12b. Alternatively, the proximal and distal portions 12a, 12b may be formed from more than two components that can overlap between the two portions 12a, 12b, or the proximal and distal portions 12a, 12b may be formed of a single unitary piece of rigid polymeric material.

Figure 2:
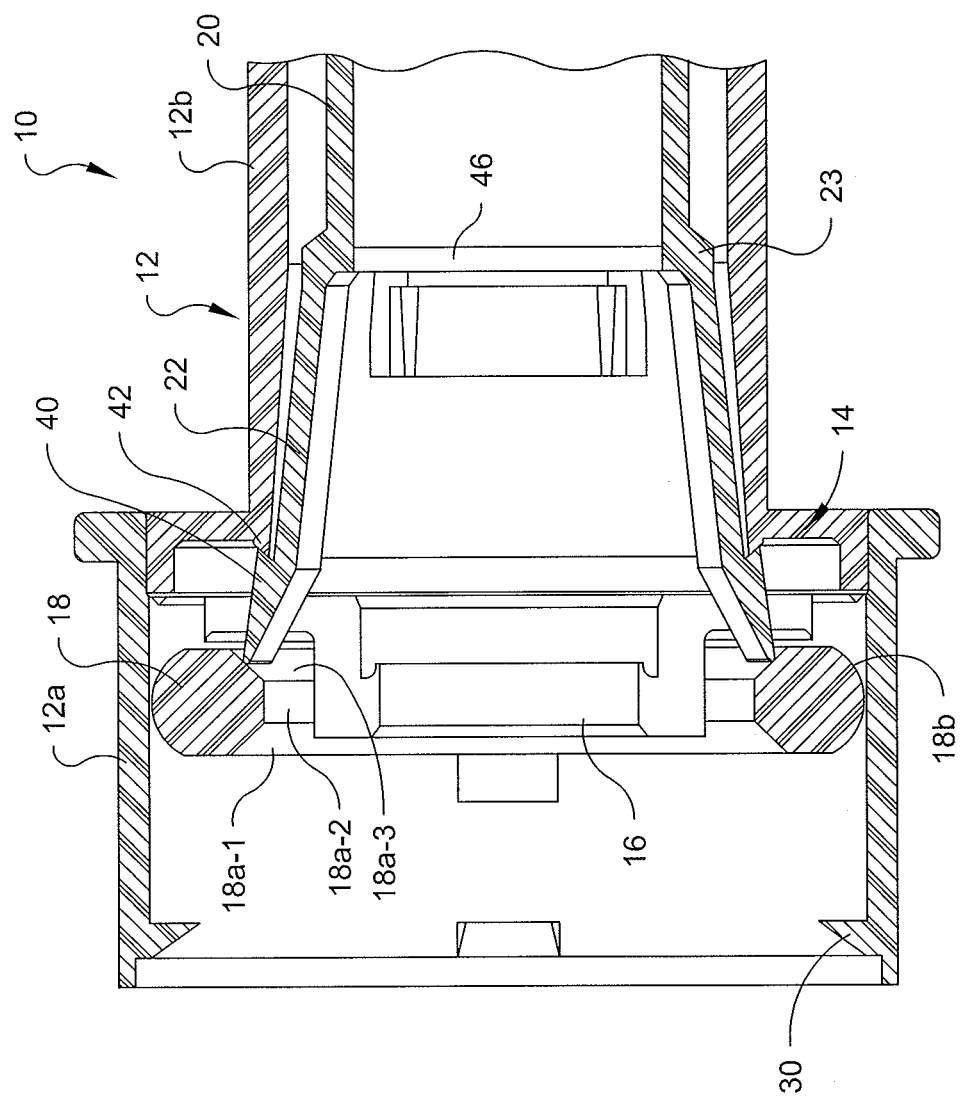
FIG. 2 is an enlarged partial cross-sectional side elevational view of the needle safety device of FIG. 1.

A ring 18 is disposed in the interior of the proximal portion 12a of the sleeve 12 and has a radial inner surface 18a and a radial outer surface 18b (FIG. 2). The ring 18 is preferably made from polyoxymethylene, although other materials may be used as well. As will be explained in more detail below, the ring 18 is movable with respect to the proximal portion 12a of the sleeve 12 in an axial direction between a first position (e.g., FIG. 4) wherein the ring 18 is axially spaced from the projecting ledge 14, and a second position (e.g., FIG. 8) wherein the ring 18 is adjacent to or abuts the projecting ledge 14. The outer surface 18b may contact an inner surface of the proximal portion 12a of the sleeve 12, however, the ring 18 should be freely movable, at least with respect to the proximal portion 12a of the sleeve 12, for reasons that will be described in more detail below.

As shown in FIG. 2, the inner surface 18a of the ring 18 preferably includes at least three portions: a proximal tapered annular portion 18a-1, an annular flat portion 18a-2, and a distal tapered annular portion 18a-3 (FIG. 2). The proximal and distal tapered portion 18a-1, 18a-3 preferably taper axially and radially away from the flat portion 18a-2, which represents a maximum diameter of the ring 18 between the inner and outer surfaces 18a, 18b.

Referring again to FIG. 1, a hollow shield 20 formed of a rigid polymeric material is at least partially disposed in the sleeve 12 and is movable with respect thereto in an axial direction. The shield 20 includes, at a proximal end, at least one, and preferably two, first latch members, preferably in the form of radially deformable tabs 22, which may be connected to the shield 20 via a living hinge 23, although other methods of connection may be used. The sleeve 12 and shield 20 are preferably circular in cross section, although other cross-sectional shapes may be used in keeping with the concept of the invention. In the embodiment shown, the two deformable tabs 22 are preferably coupled to the shield 20 at diametrically opposing sides of the circumference of the shield 20.

Figure 4:
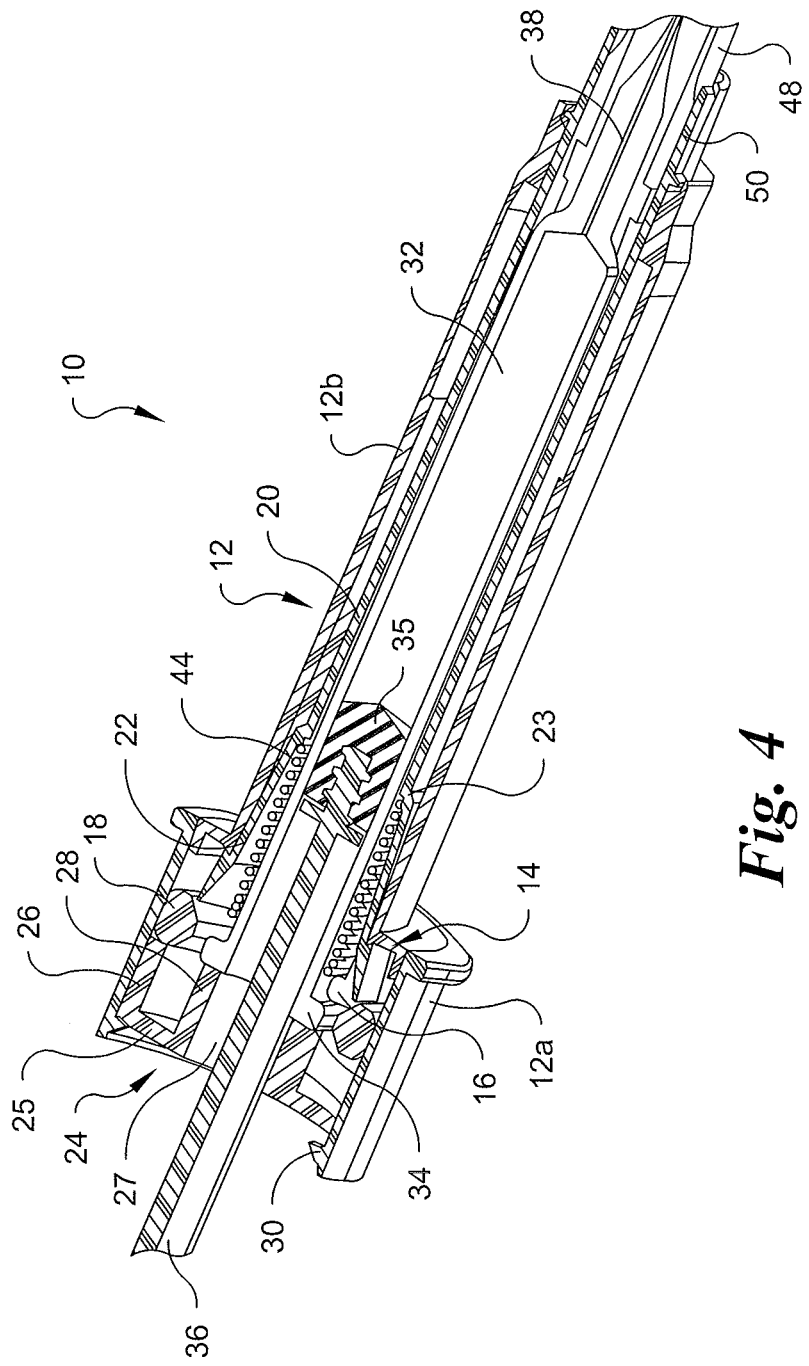
FIG. 4 is a partial cross-sectional perspective view of the needle safety device of FIG. 3 with a syringe installed therein.
Figure 5:
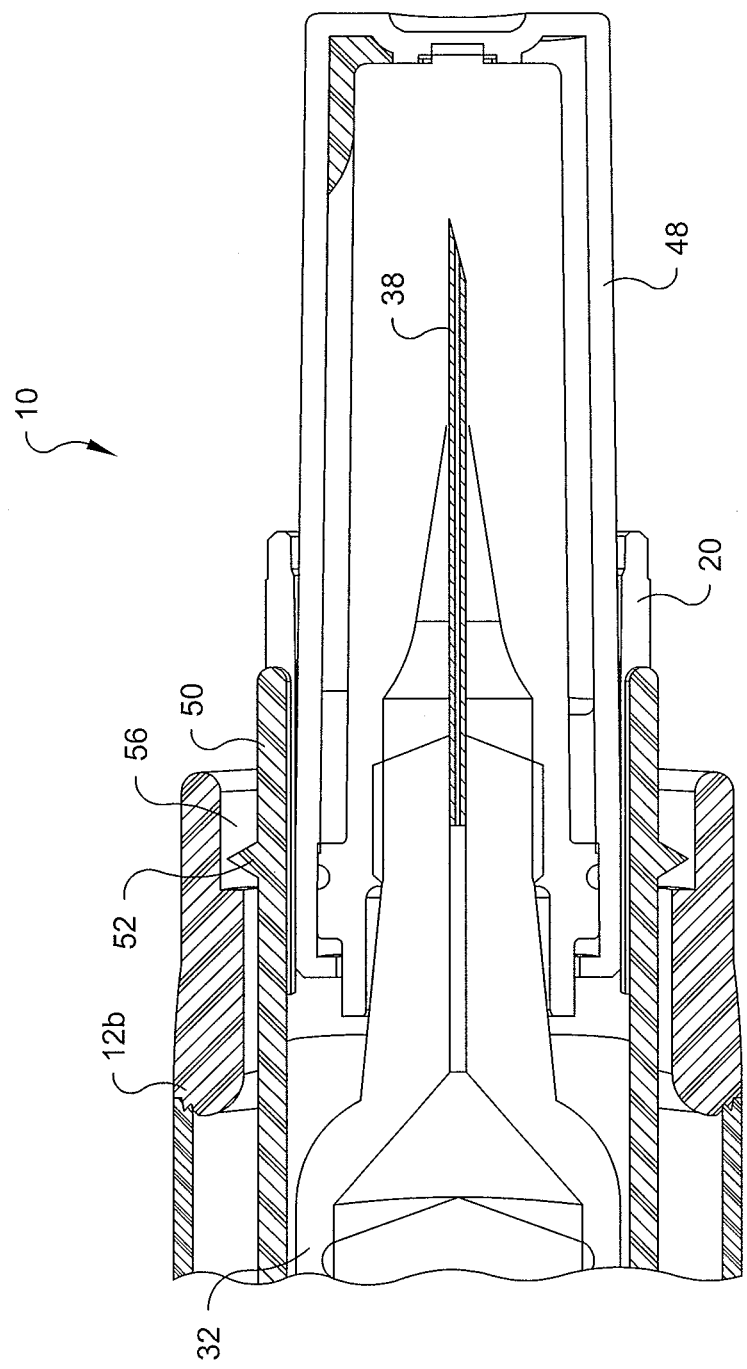
FIG. 5 is an enlarged partial cross-sectional side elevational view of the needle safety device, syringe, and cap of FIG. 4.

Referring to FIG. 4, a clip 24 made from polycarbonate or the like is preferably disposed within the proximal portion 12a of the sleeve 12. The clip 24 preferably has a proximal surface 25 with an outer skirt 26 extending therefrom around a periphery of the clip 24. One function of the clip 24 is to limit the range of motion of the ring 18. For example, when the ring 18 is in the first position (i.e., spaced from the ledge 14), the ring 18 is adjacent to or abuts the clip 24, and more particularly the outer skirt 26. The clip 24 is preferably retained within the proximal portion 12a of the sleeve 12 by one or more radially-inwardly extending protrusions 30 of the proximal portion 12a of the sleeve 12, which abut the proximal surface 25 of the clip 24 and oppose removal when the clip 24 is installed within the proximal portion 12a of the sleeve 12 as shown. The peripheral wall of the proximal portion 12a of the sleeve 12 is preferably flexible enough to allow for insertion of the clip 24. However, other methods for installing and retaining the clip 24 may be used as well.

The other function of the clip 24 is to retain a syringe 32 that is at least partially received within the shield 20. The clip 24 preferably includes an inner skirt 28 extending from the proximal surface 25 that abuts a flange 34 of the syringe 32 when the clip 24 is installed. The flange 34 is retained between the inner skirt 28 and one or more brackets 16 disposed in the proximal portion 12a of the sleeve 12. The clip 24 is therefore retained between the syringe flange 34 and the one or more protrusions 30 of the proximal portion 12a of the sleeve 12, and prevents movement of the syringe 32 in the proximal direction. The clip 24 preferably includes a slot 27 formed in the periphery and extending to a center of the proximal surface 25. The slot 27 allows the clip 24 to be installed after the syringe 32 is in place. A piston 36 of the syringe 32, used to activate a plunger 35 thereof, is received in the slot 27 when the clip is installed. Of course, other configurations of the clip 24 for retaining the syringe 32 and the ring 18 are within the scope of the invention. For example, rather than having a proximal surface 25 with extending skirts 26, 28, the clip 24 may have a solid body construction.

The shield 20 is preferably movable between three primary positions with the syringe 32 installed. In an initial position (FIG. 4), the deformable tabs 22 of the shield 20 abut the projecting ledge 14 of the sleeve 12 and the shield 20 is retracted within the sleeve 12. It is preferred that the deformable tabs 22 each include a hook 40 that mates with a corresponding catch 42 on the projecting ledge 14 (see FIG. 2). This configuration prevents distal movement of the shield 20 with respect to the sleeve 12 to maintain the shield 20 in the initial position. In an injection position (FIG. 6), the deformable tabs 22 are spaced from the projecting ledge 14 by the ring 18 and are at least partially encircled by the ring 18. The shield 20 is preferably entirely contained within the sleeve 12 when the shield 20 is in the injection position. In a final or protection position (FIG. 9), the deformable tabs 22 are located distally from the projecting ledge 14 and disposed within the distal portion 12b of the sleeve 12. As a result, the shield 20 is extended from the sleeve 12 and covers a needle 38 attached to the syringe 32.

A coil spring 44 is preferably axially disposed within the sleeve 12, and more preferably within the shield 20, to bias the shield 20 to the protection position. The spring 44 is preferably compressed between the one or more brackets 16 of the proximal portion 12a of the sleeve 12 and one or more radially-inwardly extending spring retention ledges 46 of the shield 20. Preferably, the spring retention ledges 46 are located proximate the connection point of the deformable tabs 22 (e.g., proximate the living hinge 23). The spring 44 is preferably in a compressed state when the shield 20 is in the initial and injection positions. During movement of the shield 20 to the protection position, the spring 44 relaxes and preferably disengages from the shield 20 (see FIG. 9).

Figure 3:
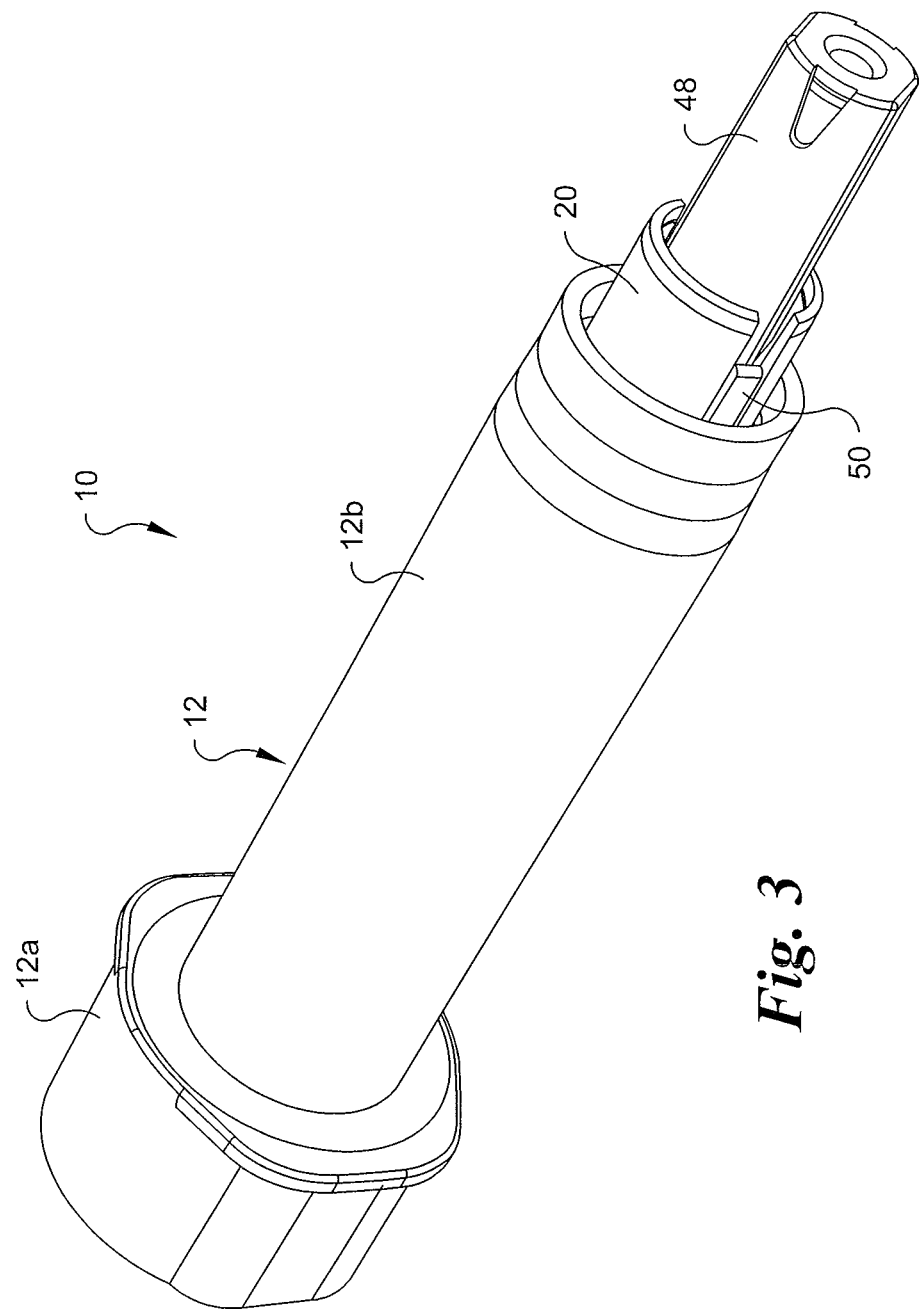
FIG. 3 is a perspective view of the needle safety device of FIG. 1 with the cap installed.

Referring to FIGS. 3 and 4, the needle safety device 10 preferably also includes a cap 48 that initially covers the needle 38 prior to use of the needle safety device 10. The cap 48 may be a conventional cap formed of an outer rigid polymeric material and an inner material, which may be rubber or other polymeric material to protect the needle 38. The cap 48 is preferably removably positioned at least partially within a distal end of the shield 20 when the shield 20 is in the initial position. Once the cap 48 is removed, the needle 38 is exposed (see FIG. 6).

The cap 48 also preferably serves to prevent accidental activation of the needle safety device 10 during shipping and storage. For example, the shield 20 at a distal end thereof may include at least one, and preferably two, second latch members preferably in the form of radially deformable fingers 50, each having a protuberance 52 extending radially-outwardly therefrom. The fingers 50 are each preferably attached to the shield 20 via a living hinge 54, although other methods of attachment may be used as well. The fingers 50 are preferably biased to a radially-inwardly deflected position (see e.g., FIG. 1) when the cap 48 is not installed in the shield 20.

The distal portion 12b of the sleeve 12 includes recesses 56 formed in an inner surface thereof. When the cap 48 is installed in the shield 20, the cap 48 urges the fingers 50 radially outwardly. The recesses 56 are configured to mate with corresponding protuberances 52 of the fingers 50. Thus, the shield 20 is locked in position and proximal relative movement of the shield 20 with respect to the sleeve 12 is prevented until the cap 48 is removed and the fingers 50 return to the rest position, i.e., the protuberances 52 are removed from the recesses 56.

Operation of the needle safety device 10 will now be described with respect to FIGS. 4-9. The needle safety device 10 begins with the shield 20 in the initial position and the cap 48 installed over the needle 38 of the syringe 32. The patient or medical professional first removes the cap 48, thereby releasing the needle 38. The fingers 50 on the shield 20 are also released and the protuberances 52 are withdrawn from the corresponding recesses 56 on the sleeve 12, thereby allowing axial movement of the shield 20 in the distal direction relative to the sleeve 12.

Figure 6:
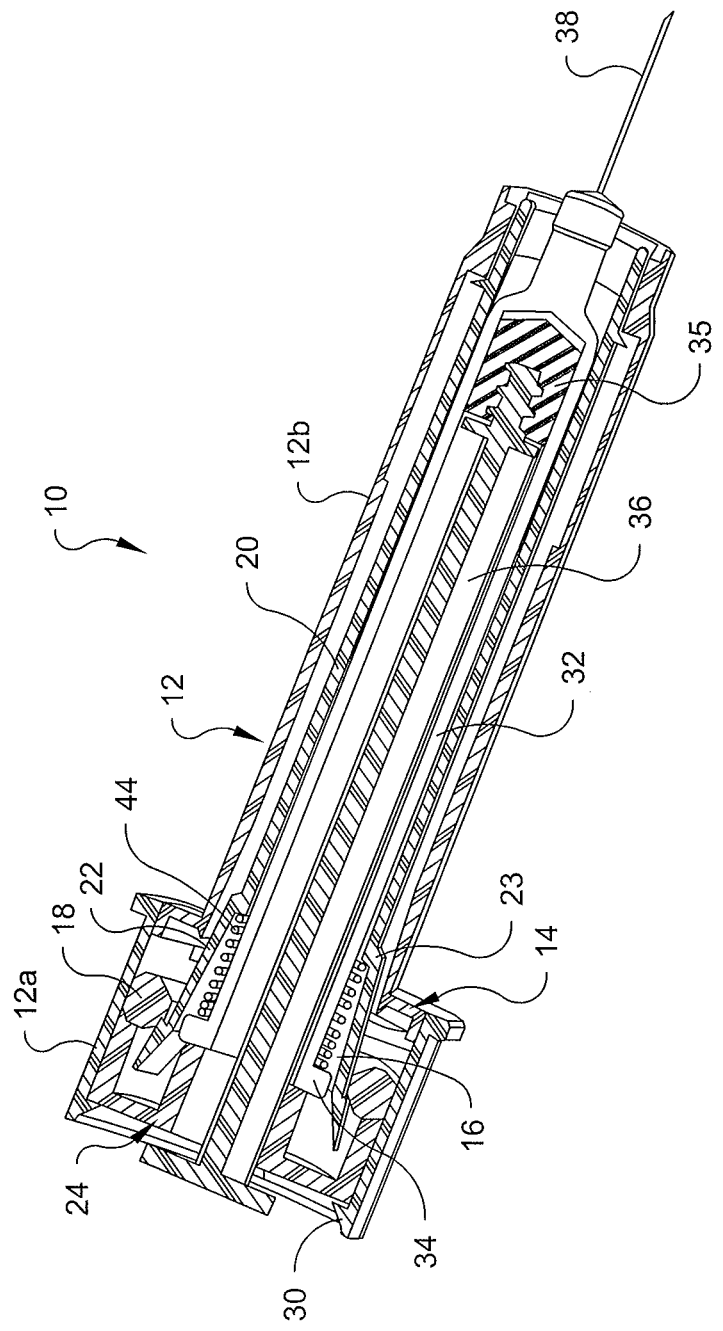
FIG. 6 is a partial cross-sectional perspective view of the needle safety device of FIG. 4 in the injection position and with the cap removed.

As the needle 38 is inserted into the skin of the patient (not shown), the distal end of the shield 20 comes into contact with the skin, and further insertion of the needle 38 causes the skin to apply a force that moves the shield 20 in a proximal direction relative to the sleeve 12 toward the injection position. The ring 18, which is in the first position, is prevented from moving proximally because of the clip 24, and therefore the deformable tabs 22 at the proximal ends thereof are deflected radially inwardly by the ring 18. For example, as the deformable tabs 22 traverse the distal tapered portion 18a-3 of the inner surface 18a of the ring 18, the deformable tabs 22 are urged radially inwardly, allowing the deformable tabs 22 to enter and traverse the entirety of the inner surface 18a of the ring 18 and to release the hooks 40 from the catches 42. The relative motion of the shield 20 with respect to the sleeve 12 as well as the syringe 32 causes further compression of the spring 44. As shown in FIG. 6, when the needle 38 is fully inserted into the skin, proximal motion of the shield 20 ceases and the plunger 35 may be actuated to dispense the medicament into the patient.

Figure 7:
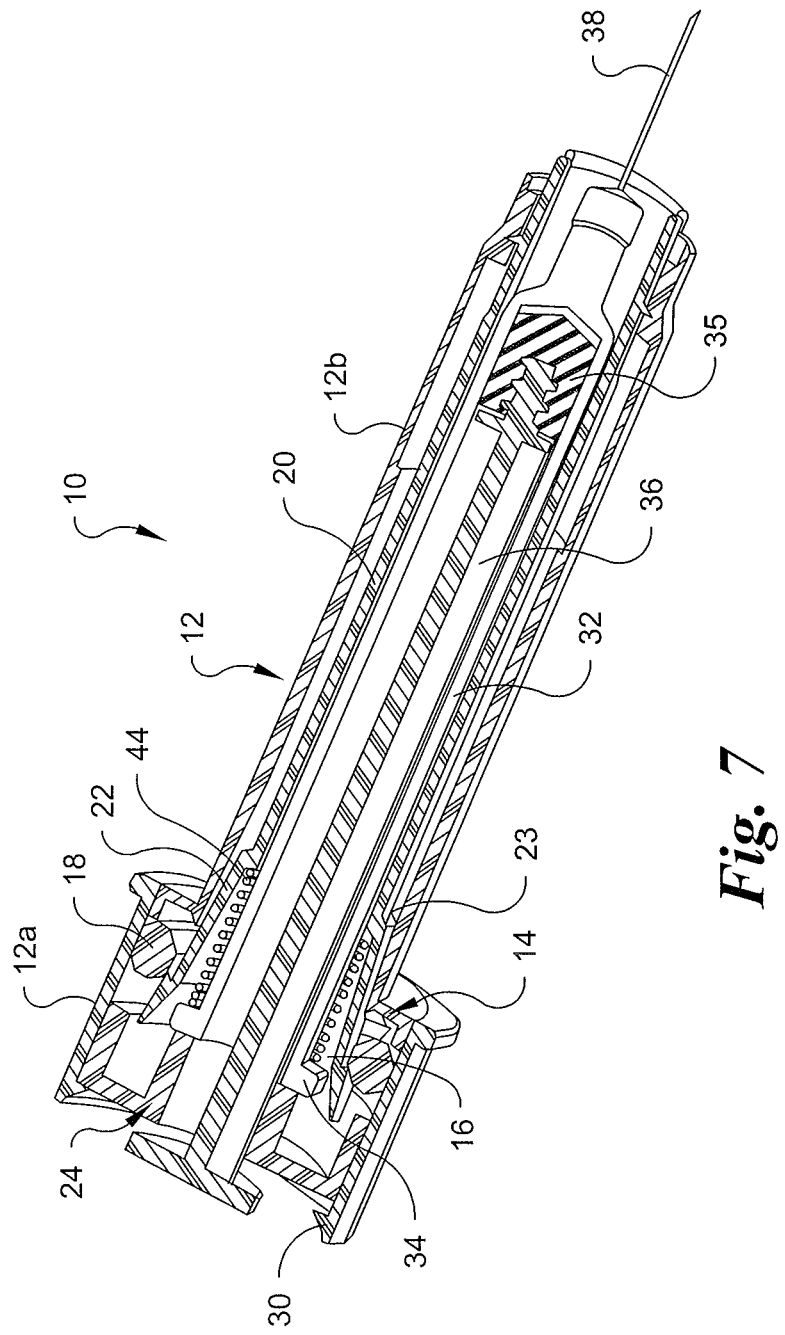
FIG. 7 is a partial cross-sectional perspective view of the needle safety device of FIG. 6 in transition from the injection position to a protection position.

Referring to FIG. 7, as the needle 38 is withdrawn from the patient, the force of the compressed spring 44 causes the shield 20 to move in a distal direction with respect to the sleeve 12 and syringe 32. Consequently, the deformable tabs 22 exert a force on the ring 18 and pull the ring 18 distally within the proximal portion 12a of the sleeve, thereby moving the ring 18 toward the second position. The shield 20 and the ring 18 translate together until the ring 18 bottoms out by abutting the projecting ledge 14.

Figure 8:
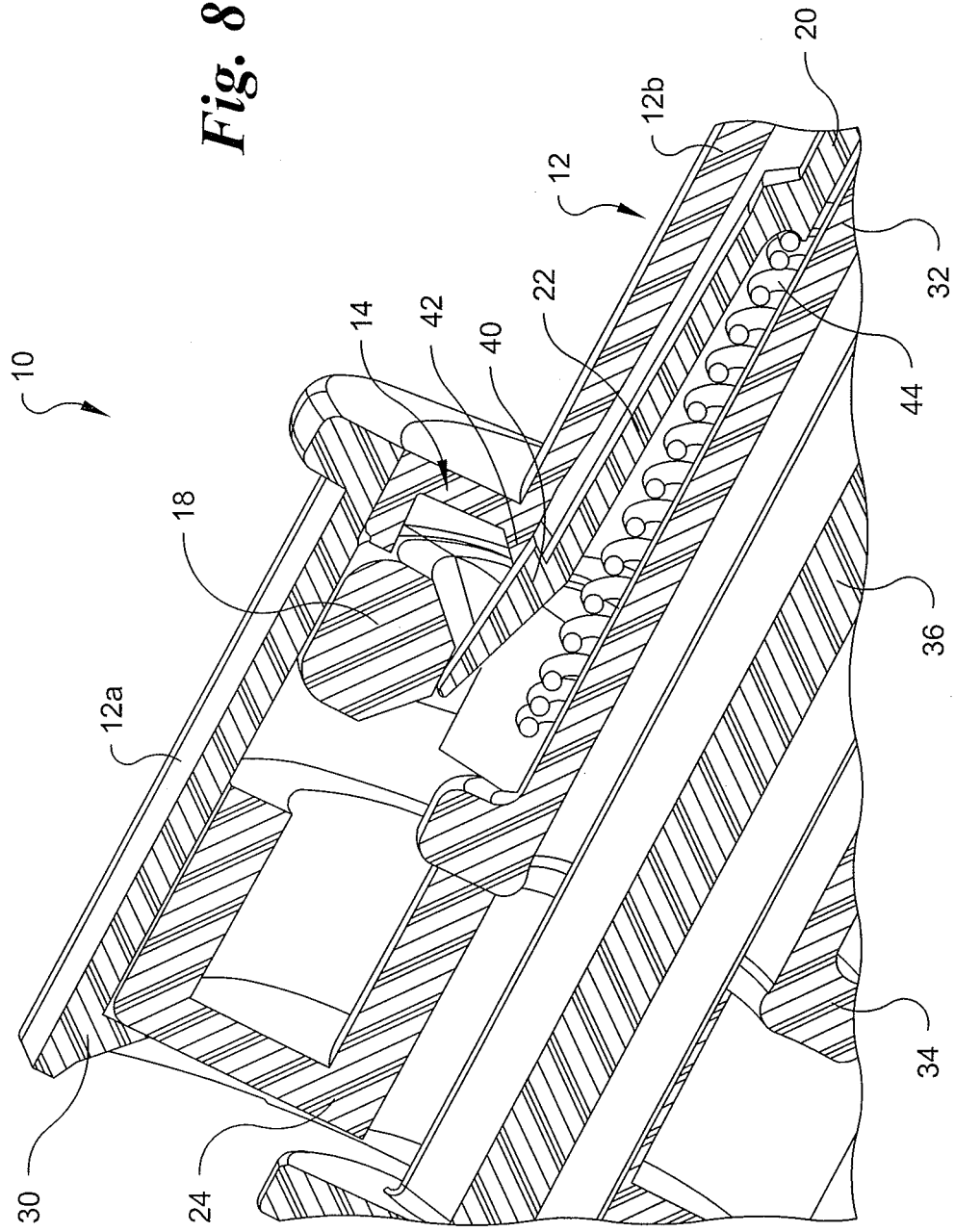
FIG. 8 is an enlarged partial cross-sectional perspective view of the needle safety device and syringe of FIG. 7.

Referring to FIG. 8, once the ring 18 abuts the projecting ledge 14, further distal movement of the ring 18 within the sleeve 12 is prevented by the projecting ledge 14, but the energy of the spring 44 continues to urge the shield 20 forward. Thus, the deformable tabs 22 are deflected radially inwardly again as the deformable tabs 22 traverse the proximal tapered portion 18a-1 of the inner surface 18a of the ring 18, enabling the deformable tabs 22 to traverse the entirety of the ring 18. With the ring 18 in the second position, however, the deformable tabs 22 cannot return to the initial position abutting the projecting ledge 14. Rather, the hooks 40 traverse past the corresponding catches 42 and the deformable tabs 22 fully enter into the distal portion 12b of the sleeve 12.

Figure 9:
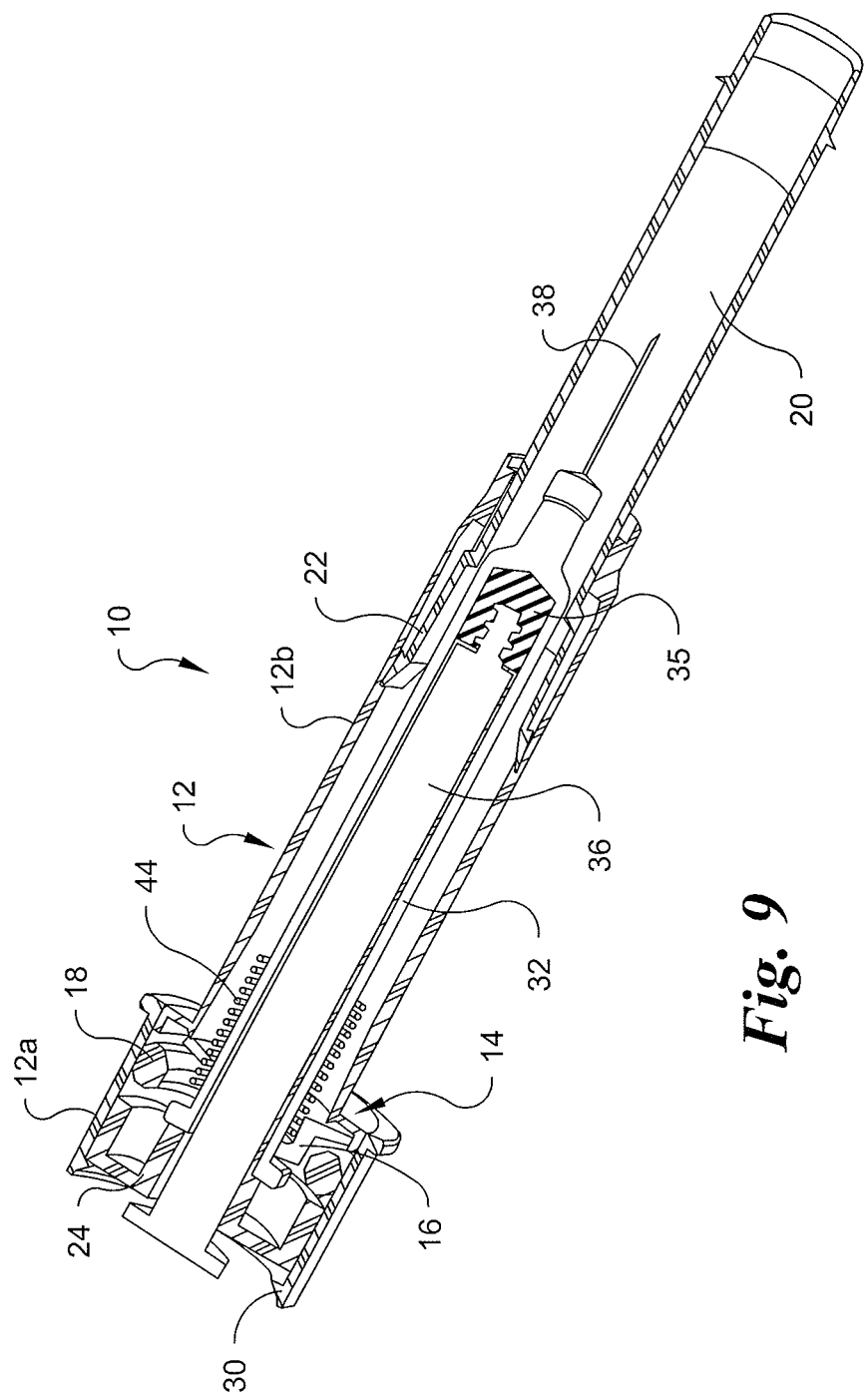
FIG. 9 is a partial cross-sectional perspective view of the needle safety device of FIG. 7 in the protection position.

Referring to FIG. 9, the shield 20 continues distal movement with respect to the sleeve 12 until the needle 38 is adequately covered and retained by the shield 20 in the protection position. Additional recesses or radially-inwardly projecting ledges (not shown) may be provided in the sleeve 12 to oppose removal of the shield 20 from the sleeve and/or movement proximally back into the sleeve 12, either of which would undesirably expose the needle 38. Thus, the needle safety device 10 is automatically activated by the actions of contact and removal of the device 10 from the skin of the patient during injection.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

What is claimed is:

1. A needle safety device for a syringe having a barrel and a needle fitted to a distal end of the barrel, the device comprising:
   a hollow sleeve having a proximal portion and a distal portion, the proximal portion being separated from the distal portion by a radially-inwardly projecting ledge;
   a ring disposed in the proximal portion of the sleeve and having an outer surface and an inner surface, the ring being movable with respect to the proximal portion of the sleeve in an axial direction between a first position wherein the ring is spaced from the projecting ledge, and a second position, wherein the ring is adjacent to or abuts the projecting ledge;
   a hollow shield configured to receive the syringe at least partially therein and having at least one radially deformable tab at a proximal end thereof, the shield being at least partially disposed in the sleeve and being movable in an axial direction with respect to the sleeve between an initial position wherein the at least one tab is adjacent to or abuts the projecting ledge, an injection position wherein the at least one tab is spaced from the projecting ledge, and a protection position wherein the at least one tab is located distally from the projecting ledge so that the shield covers the needle, the at least one tab being configured to:
      (i) during movement between the initial position and the injection position, deform radially inwardly and traverse the inner surface of the ring in the first position,
      (ii) during movement between the injection position and the protection position, translate with the ring from the first position to the second position, and subsequently deform radially inwardly and traverse the inner surface of the ring and the projecting ledge.

2. The device of claim 1, further comprising a cap removably positioned at least partially within a distal end of the shield to cover the needle when the shield is in the initial position, the cap being removable to expose the needle.

3. The device of claim 2, wherein the shield at the distal end thereof includes at least one radially deformable finger having a protuberance extending radially therefrom.

4. The device of claim 3, wherein when the cap is positioned within the shield, an outer surface of the cap urges the at least one finger radially outwardly.

5. The device of claim 4, wherein the sleeve includes at least one recess formed in the distal portion thereof, the at least one recess being configured to mate with the protuberance of the at least one finger when the at least one finger is urged radially outwardly by the cap, such that the at least one recess prevents relative movement of the sleeve and the shield toward the injection position.

6. The device of claim 5, wherein when the cap is removed, the protuberance is released from the at least one recess.

7. The device of claim 1, further comprising a clip disposed within the proximal portion of the sleeve.

8. The device of claim 7, wherein the ring is adjacent to or abuts the clip when the ring is in the first position.

9. The device of claim 1, wherein the at least one tab includes a hook, and the ledge includes at least one catch that mates with the hook when the sleeve and the shield are in the initial position.

10. The device of claim 1, further comprising a spring mounted within the sleeve that biases the shield to the protection position.

11. The device of claim 1, wherein the inner surface of the ring is tapered such that the at least one tab is urged radially inwardly while the at least one tab traverses the inner surface of the ring.

12. The device of claim 1, wherein when the sleeve and the shield are in the injection position, the shield is entirely contained within the sleeve.

13. A needle safety device for use with a syringe having a barrel and a cannula extending from the barrel, comprising:
    a body;
    a ring supported by the body and movable relative to the body;
    a shield supported by the body and movable between an initial retracted position and a final extended position relative to the body;
    at least one first latch member extending from the shield; and
    a spring in contact with both the body and the shield, the spring biasing the shield toward the final extended position,
wherein:
    in a first configuration, the shield is in the initial retracted position and the at least one first latch member engages the body to retain the shield against the bias of the spring,
    in a second configuration, contact of a distal end of the shield against an injection site moves the shield relative to the body, moving the at least one first latch member into engagement with the movable ring and releasing the at least one first latch member from engagement with the body,
    in a third configuration, with the distal end of the shield moved out of contact with the injection site, the spring moves the movable ring and shield relative to the body, with the movable ring holding the at least one first latch member to prevent the at least one first latch member from re-engaging the body; and
    in a fourth configuration, the shield is moved by the spring into the final extended position covering the cannula.

14. The needle safety device of claim 13, the shield further comprising at least one second latch member having an engaged position and a disengaged position, wherein in the engaged position the at least one second latch member engages the body to prevent movement of the shield relative to the body, thus preventing movement from the first to the second configuration, and in the disengaged position the at least one second latch member disengages from the body to allow movement of the shield relative to the body, allowing movement from the first configuration to the second configuration.

15. The needle safety device of claim 14, wherein the at least one second latch member is biased toward the disengaged position.

16. The needle safety device of claim 15, wherein the at least one second latch member is held in the engaged position by a needle tip cap.

17. The needle safety device of claim 16, wherein removal of the needle tip cap enables the at least one second latch member to move from the engaged position to the disengaged position.

18. The needle safety device of claim 13, wherein in the fourth configuration, the at least one first latch member engages the body to lock the needle safety shield in the extended position covering the cannula.

* * * * *